(12) United States Patent
Doyle

(10) Patent No.: US 9,505,825 B2
(45) Date of Patent: Nov. 29, 2016

US009505825B2

(54) METHODS AND SYSTEMS FOR ZINC DELIVERY USING INTRINSIC FACTOR OR HAPTOCORRIN

(71) Applicant: Syracuse University, Syracuse, NY (US)

(72) Inventor: Robert P. Doyle, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 14/891,412

(22) PCT Filed: May 15, 2014

(86) PCT No.: PCT/US2014/038220
§ 371 (c)(1),
(2) Date: Nov. 16, 2015

(87) PCT Pub. No.: WO2014/186587
PCT Pub. Date: Nov. 20, 2014

(65) Prior Publication Data
US 2016/0083451 A1    Mar. 24, 2016

Related U.S. Application Data

(60) Provisional application No. 61/823,594, filed on May 15, 2013.

(51) Int. Cl.
| | |
|---|---|
| *C07K 14/795* | (2006.01) |
| *A61K 33/30* | (2006.01) |
| *A61K 47/48* | (2006.01) |
| *C07K 14/47* | (2006.01) |

(52) U.S. Cl.
CPC ............ *C07K 14/795* (2013.01); *A61K 33/30* (2013.01); *A61K 47/48246* (2013.01); *C07K 14/47* (2013.01); *C07K 2319/00* (2013.01); *C07K 2319/20* (2013.01)

(58) Field of Classification Search
None
See application file for complete search history.

(56) References Cited

U.S. PATENT DOCUMENTS

2002/0028769 A1    3/2002    Ji

FOREIGN PATENT DOCUMENTS

| WO | 0196372 | 12/2001 |
|---|---|---|
| WO | 2007070936 | 6/2007 |

OTHER PUBLICATIONS

Chaturvedi et al. Cloning and transcript analysis of type 2 metallothionein gene (SbMT-2) from extreme haplohyte Salicornia brachiata and its heterologous expression in E. coli. Gene, vol. 499, pp. 280-287, Mar. 14, 2012.*
Carmel et al. Genomic mutations associated with mild and severe deficiencies of transcobalamin I (haptocorrin) that cause mildly and severely low serum cobalamin levels. British Journal of Haematology, vol. 147, pp. 386-391, 2009.*
Wong et al. Evaluation of a structural model of Pseudomonas aeruginosa outer membrane protein OprM, an efflux component involved in intrinsic antibiotic resistance. Journal of Bacteriology, vol. 183, No. 1, pp. 367-374, Jan. 2001.*
Fedosov, S.N. et al., "Comparative Analysis of Cobalamin Binding Kinetics and Ligand Protection for Intrinsic Factor, Transcobalamin, and Haptocorrin", J. Biol. Chem., vol. 277, No. 12, pp. 9989-9996, see abstract: p. 9989, left column; figures 2-5, Mar. 2002.
International Search Report Form PCT/ISA/220, International Application No. PCT/US2014/038220, pp. 1-14, Dated Oct. 27, 2014.
Wuerges, J. et al., May 1, 2007, "Structural Study on Ligand Specificity of Human Vitamin B12 Transporters", Biochemical Journal, vol. 403, No. 3, pp. 431-440, see abstract: figures 1-4.

* cited by examiner

*Primary Examiner* — Jennifer Dunston
(74) *Attorney, Agent, or Firm* — Bond Schoeneck and King PLLC; David Nocilly; George McGuire

(57) ABSTRACT

Improved delivery of zinc using haptocorrin or intrinsic factor modified to include a zinc binding sequence that can outcompete dietary zinc inhibitors such as phytin. Known zinc binding sequences can be assayed to determine competitiveness with respect to phytin and, if successful, incorporated into the $B_{12}$ binding site of haptocorrin or intrinsic factor. Thus a method of producing functional human haptocorrin or intrinsic factor which binds to zinc includes the steps of modifying human TCN1 or GIF to comprise one or more zinc-binding site sequences, constructing a vector containing the modified human TCN1 or GIF sequence, and introducing the vector into a host cell for a time and under conditions sufficient for expression of the functional human haptocorrin or intrinsic factor. The resulting zinc binding complex can be orally administered to zinc deficient individuals to improve the amount of dietary zinc available to the individuals.

8 Claims, 4 Drawing Sheets

METHODS AND SYSTEMS FOR ZINC DELIVERY USING INTRINSIC FACTOR OR HAPTOCORRIN

CROSS-REFERENCE TO RELATED APPLICATIONS

This application claims priority to U.S. Provisional Patent Application Ser. No. 61/823,594, filed on May 15, 2013, and entitled "Zinc Delivery System Using Intrinsic Factor or Haptocorrin," the entire disclosure of which is incorporated herein by reference.

BACKGROUND

The present invention relates to methods and systems for oral delivery of zinc and, more specifically, to the use of intrinsic factor or haptocorrin to enhance oral zinc delivery and zinc absorption.

Zinc deficiency is widespread and affects the health and well-being of populations worldwide. As much as 25% of the world's population may have inadequate levels of zinc in their diet due to a combination of factors including limited access to zinc-rich foods such as animal products, oysters, or shellfish, and the abundance of zinc inhibitors such as phytin that are common in plant-based foods. Thus, even if an individual's zinc intake levels are adequate, the levels of inhibitors in the diet through consumption of foods such as cereals, corn, and rice may mean that inadequate amounts of zinc are absorbed. As a result, zinc deficiency may not necessarily be treated by providing dietary zinc supplements or increasing the amount of zinc rich foods consumed by individuals having diets comprised of foods containing zinc inhibitors.

A human being with adequate levels of zinc comprises 2-4 grams of the mineral dispersed throughout their body, with major concentrations found in the brain, muscles, and bones. Zinc is utilized by the human body in a wide array of different metabolic processes, including the metabolism of RNA and DNA, signal transduction, gene expression, apoptosis, and, perhaps most importantly, the structure and function of proteins such as enzymes.

Insufficient levels of zinc in the body, however, can have devastating effects ranging from minor to devastating. Minor side-effects of low zinc levels include diarrhea, acne, and low testosterone, while major issues include cognitive and motor function impairment, chronic renal disease, and the malfunction of processes such as eyesight, memory, and smell, among many others. As a result, zinc deficiency can result in significant reduction of quality of life, leading even to increased mortality rates.

Accordingly, there is a need in the art for methods and systems that facilitate zinc supplementation in a manner that avoids dietary zinc inhibitors and provides an adequate amount of zinc to be absorbed by a zinc-deficient individual.

BRIEF SUMMARY

The present invention is directed to methods and systems to enhance oral zinc delivery and zinc absorption using intrinsic factor or haptocorrin. In view of the foregoing, embodiments are directed to a system of protecting orally delivered zinc from degradation using intrinsic factor bound to the zinc. Known zinc binding sequences are tested for competitiveness against phytin, and successful sequences are incorporated into haptocorrin or intrinsic factor, such as in a $B_{12}$ binding location since the ability to bind $B_{12}$ is not a priority. The resulting zinc binding complex may then be orally administered to zinc deficient populations to increase the amount of available supplemental or dietary zinc.

Generally, in one aspect, a nucleic acid molecule comprises a chimeric gene derived from human haptocorrin comprising a first sequence encoding a first region of haptocorrin, a second sequence encoding a zinc-binding site, and a third sequence encoding a second region of haptocorrin.

In some embodiments, the molecule is selected from the group consisting of SEQ ID NO: 1 and SEQ ID NO: 4.

In some embodiments, the zinc-binding site is inserted within an α domain of the human haptocorrin.

In some embodiments, the zinc-binding site is inserted between an α domain and a β domain of the human haptocorrin.

Generally, in one aspect, a polypeptide comprises a chimeric protein derived from human haptocorrin, the polypeptide comprising a zinc-binding site located between a first region of haptocorrin and a second region of haptocorrin.

In some embodiments, the polypeptide is selected from the group consisting of SEQ ID NO: 3 and SEQ ID NO: 6.

In some embodiments, the polypeptide is capable of reversibly binding zinc.

Generally, in one aspect, a nucleic acid molecule comprises a chimeric gene derived from human intrinsic factor comprising a first sequence encoding a first region of intrinsic factor, a second sequence encoding a zinc-binding site, and a third sequence encoding a second region of intrinsic factor.

Generally, in one aspect, a polypeptide comprises a chimeric protein derived from human intrinsic factor, the polypeptide comprising a zinc-binding site located between a first region of intrinsic factor and a second region of intrinsic factor.

Generally, in one aspect, a method of producing functional human haptocorrin which binds to zinc includes the steps of: modifying human TCN1 to comprise one or more zinc-binding site sequences; constructing a vector comprising the modified human TCN1; and introducing the vector into a host cell for a time and under conditions sufficient for expression of the functional human haptocorrin.

In some embodiments, the modified human TCN1 is selected from the group consisting of SEQ ID NO: 1 and SEQ ID NO: 4.

In some embodiments, the functional human haptocorrin comprises a polypeptide sequence selected from the group consisting of SEQ ID NO: 3 and SEQ ID NO: 6.

In some embodiments, the method further includes the step of isolating the expressed functional human haptocorrin.

In some embodiments, the method further includes the step of incubating the isolated human haptocorrin with zinc.

Generally, in one aspect, a method of producing functional human intrinsic factor which binds to zinc includes the steps of: modifying human GIF to comprise one or more zinc-binding site sequences; constructing a vector comprising the modified human GIF; and introducing the vector into a host cell for a time and under conditions sufficient for expression of the functional human intrinsic factor.

In some embodiments, the method further includes the step of isolating the expressed functional human intrinsic factor.

In some embodiments, the method further includes the step of incubating the isolated human intrinsic factor with zinc.

Generally, in one aspect, a method for testing the zinc binding affinity of a modified human haptocorrin, the method inclusion the steps of: modifying human TCN1 to comprise one or more zinc-binding site sequences; constructing a vector comprising the modified human TCN1; introducing the vector into a host cell for a time and under conditions sufficient for expression of the functional human haptocorrin; isolating the expressed functional human haptocorrin; incubating the isolated human haptocorrin with zinc; exposing the zinc-bound haptocorrin to a zinc-binding compound; and determining the effect of exposure to the zinc-binding compound on the exposed haptocorrin.

In some embodiments, the zinc-binding compound is a phytate.

In some embodiments, the exposing step is performed under conditions comprising a pH of 3 or lower.

Generally, in one aspect, a method of binding and releasing zinc using a chimeric protein includes the steps of: providing a chimeric protein derived from human haptocorrin, the chimeric protein comprising a zinc-binding site located between a first region of haptocorrin and a second region of haptocorrin; binding the polypeptide to zinc; and administering the zinc-bound polypeptide orally.

In some embodiments, the chimeric protein is selected from the group consisting of SEQ ID NO: 3 and SEQ ID NO: 6.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

Figure 1:
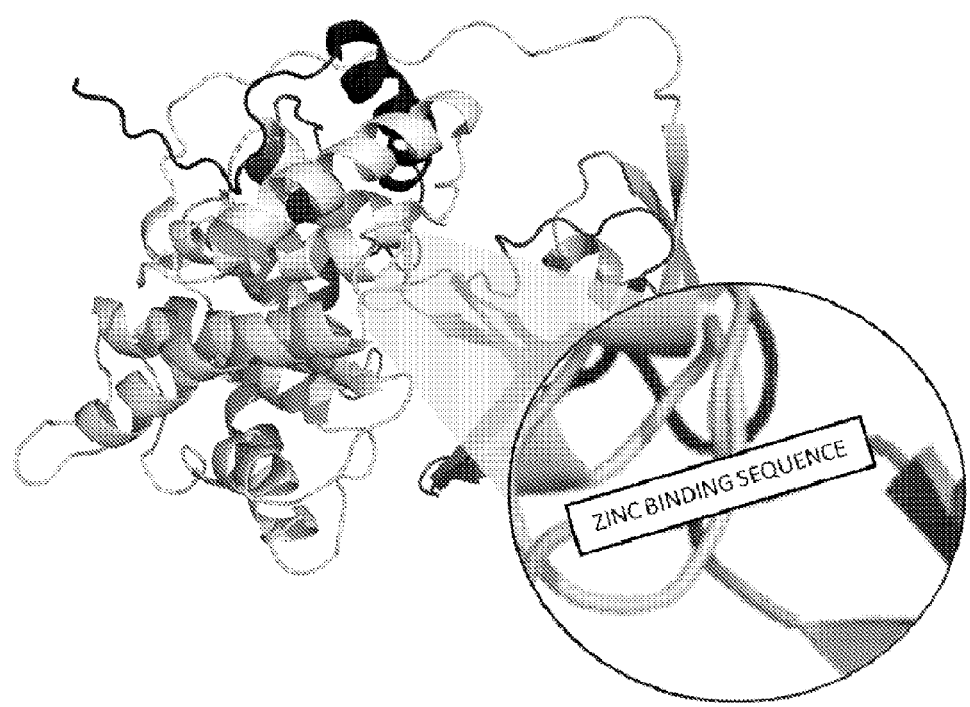
FIG. 1 is a schematic of intrinsic factor modified for the delivery of zinc according to the present invention.

It is often desirable to provide zinc supplements to zinc-deficient individuals. Prevalent zinc deficiency affects the health and well-being of millions of people around the world. Not only do people have inadequate levels of zinc in their diet due to limited access to zinc-rich foods, but the abundance of zinc inhibitors common in plant-based foods block ingested zinc. As a result, zinc deficiency may not necessarily be treated by providing dietary zinc supplements or increasing the amount of zinc rich foods consumed by individuals having diets comprised of foods containing zinc inhibitors.

In light of pervasive zinc deficiency caused by both limited access to zinc-rich foods and the abundance of zinc inhibitors, Applicants have recognized that it is desirable to provide zinc supplementation to zinc-deficient individuals in a manner that avoids dietary zinc inhibitors.

In view of the foregoing, various embodiments are directed to methods and systems to enhance oral zinc delivery and zinc absorption using intrinsic factor or haptocorrin. In particular, orally delivered zinc is protected from degradation using intrinsic factor bound to the zinc. For example, known zinc binding sequences are tested for competitiveness against phytin, and successful sequences are incorporated into haptocorrin or intrinsic factor, such as in a B12 binding location since the ability to bind B12 is not a priority. The resulting zinc binding complex may then be orally administered to zinc deficient populations to increase the amount of available supplemental or dietary zinc.

Modifying Intrinsic Factor to Bind Zinc

According to one embodiment, the structure of intrinsic factor ("IF") is modified to include a zinc binding sequence that will capture zinc and protect it from complexation with dietary phytates and other zinc inhibitors. Un-modified IF is a 43,420 Da glycoprotein produced from the GIF gene, and consisting of approximately 399 amino acids with an additional 17 of those amino acids at the N-terminus acting as a secretory signal sequence that is cleaved during processing. The structure of human IF ("hIF") is composed of α and β heterodomains, where the α domain consists of approximately 270 residues (7-273) and the β domain consists of approximately 110 residues (274-399). The α domain is composed of an $α_6/α_6$ helical barrel, while the β domain consists of β strands.

The one or more zinc binding sequences in the modified IF will capture zinc and then protect that bound zinc from other agents such as dietary phytates and other zinc inhibitors. The zinc-bound IF will travel substantially unaffected through the stomach and into the small intestine. Once in the small intestine, the complex will bind to the IF receptor expressed on epithelial cells of the ileum wall. The activated IF receptor complex then undergoes endocytosis, releasing the zinc into the blood serum. Accordingly, it is important that the modified IF not only be able to bind zinc, but must also bind and activate the IF receptor in the ileum.

Referring to FIG. 1, an embodiment of the present invention comprises a modification to IF to replace or augment at least a portion of the interface region between the a and 13 heterodomains with a zinc binding sequence. More particularly, an embodiment of the present invention comprises replacement of one or more amino acids that lie closest to the interface between the α domain (residues 7-273) and the β domain (residues 274-399), and preferably just within the beginning of the β domain. This region of IF is responsible for $B_{12}$ binding, which is not necessary for the present invention.

Modifying Haptocorrin to Bind Zinc

According to another embodiment, the structure of haptocorrin is modified to include a zinc binding sequence that will capture zinc and protect it from degradation. Unmodified haptocorrin is one of three $B_{12}$ transport proteins and is a 47 kDa, highly glycosolated, protein responsible for initial $B_{12}$ binding and transport from the mouth, through the stomach, to the intestine. Once in the intestine, haptocorrin is degraded due to an increase in pH and enzymatic digestion by trypsin and chymotrypsin, and the bound $B_{12}$ is thus released. Haptocorrin is also present in the blood serum and is hypothesized to remove $B_{12}$ analogs that are not able to successfully undergo the body's metabolic pathways. Haptocorrin includes an α domain comprised of a helical barrel (residues 1-287) and a β domain comprised of strands (residues 309-410) that are interconnected by a flexible linker.

EXAMPLE 1

Modified Haptocorrin Sequence

Figure 2:
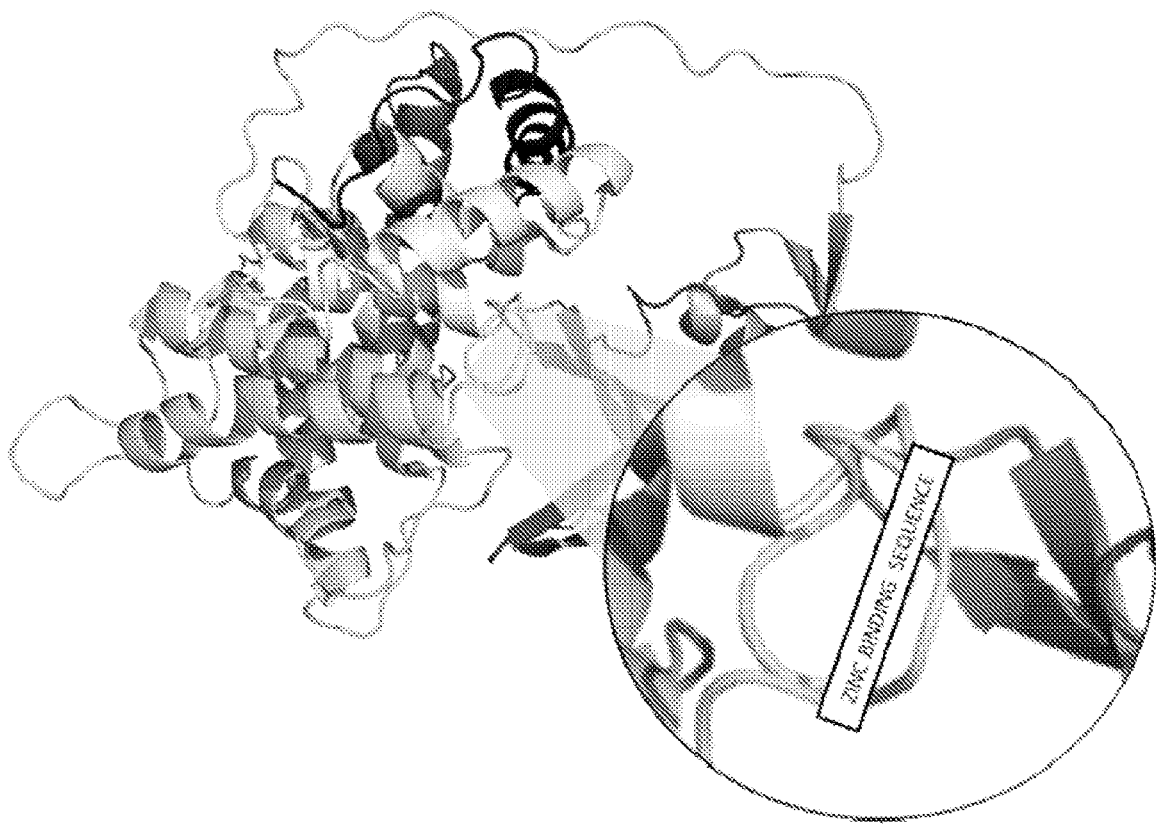
FIG. 2 is a schematic of haptocorrin modified for the delivery of zinc according to the present invention.

Referring to FIG. 2, another embodiment of the present invention comprises the modification of haptocorrin to replace at least a portion of the α-β interface region between the a domain (residues 1-287) and the β domain (309-410) with a zinc binding sequence. As with IF, this portion of haptocorrin is responsible for $B_{12}$ binding, which is not necessary for the present invention.

EXAMPLE 2

Selection of Zinc Binding Sequences

Traditional zinc-binding domains that rely on histidine and cysteine for metal coordination, such as two invariant pairs of cysteine and histidine that coordinate a zinc atom, are not efficient below a pH of 3. As a result, in accordance with an embodiment the present invention relies on polycarboxylate coordination using the side chains of Asp and Glu. Polyaspartate tags are well-established effective metal chelators and will likely provide enough stability, even at a low pH. Specifically, in accordance with one embodiment, the present invention encompasses the following sequences:

G/A-(XG)n

G-((X3)G(X3))m-G

Xo where X=Glu or Asp; n=4-7; m=2-3; and o=6-10, although many other variations and zinc-binding sequences are possible.

Zinc binding sequences may be evaluated to determine their binding affinities (Kd) to zinc, particularly with regard to the binding affinity of phytin to zinc. Sequences having a sufficiently high or higher affinity for zinc than phytin may be inserted into the predetermined location of haptocorrin or IF, and then subjected to a phytin challenge to determine whether the test complex can outcompete phytin for zinc. This challenge can be performed in vitro and is preferably done at a pH of 2-3 to replicate the acid environment of the intestines.

EXAMPLE 3

Location of Zinc Binding Sequences

Selecting the location within haptocorrin and intrinsic factor to insert the one or more zinc-binding sequences is also vital to the successful structure and function of the modified protein, including both zinc-binding and protection of the zinc as the protein travels through the stomach and into the small intestine. The selected location must result in a stable protein that can bind zinc and protect it from the environment of the stomach.

Preferably, for modified haptocorin for example, the selected location should result in a stable protein that is also capable of binding vitamin $B_{12}$ in addition to the zinc. For example, the modified haptocorrin can bind the zinc in the bottom of the vitamin $B_{12}$ pocket and then the vitamin $B_{12}$ can subsequently bind within the pocket, providing additional protection. Haptocorrin consists of an α domain comprised of a helical barrel (residues 1-287) and a β domain comprised of β strands (residues 309-410) that are interconnected by a flexible linker. According to one embodiment, the one or more zinc binding site sequences are inserted within the haptocorrin gene such that the binding site is at the bottom of the $B_{12}$ binding site, located at the bottom of the α domain, where the zinc will be highly protected. That location will also avoid disruption of $B_{12}$ binding, allowing $B_{12}$ to bind to the pocket on top of the zinc which provides further protection. According to another embodiment, the one or more zinc binding site sequences are inserted within the haptocorrin gene such that the binding site is at the loop between the α domain and a β domain.

EXAMPLE 4

Modified Haptocorrin Sequence 1 (YNHCZn)

As described herein, and in accordance with an embodiment, the human haptocorrin protein encoded by the TCN1 gene can be modified to include one or more zinc-binding sites. For example, SEQ ID NO: 1 is an example of the modified TCN1 gene containing the zinc-binding site sequence RDADADR (SEQ ID NO: 2) (a common zinc-binding site sequence), and which results in expression of the modified human haptocorrin protein identified by SEQ ID NO: 3. According to this embodiment, the 21-nucleotide sequence for the zinc-binding "RDADADR" sequence is inserted between nucleotides 423 and 424 of human haptocorrin.

Figure 3:
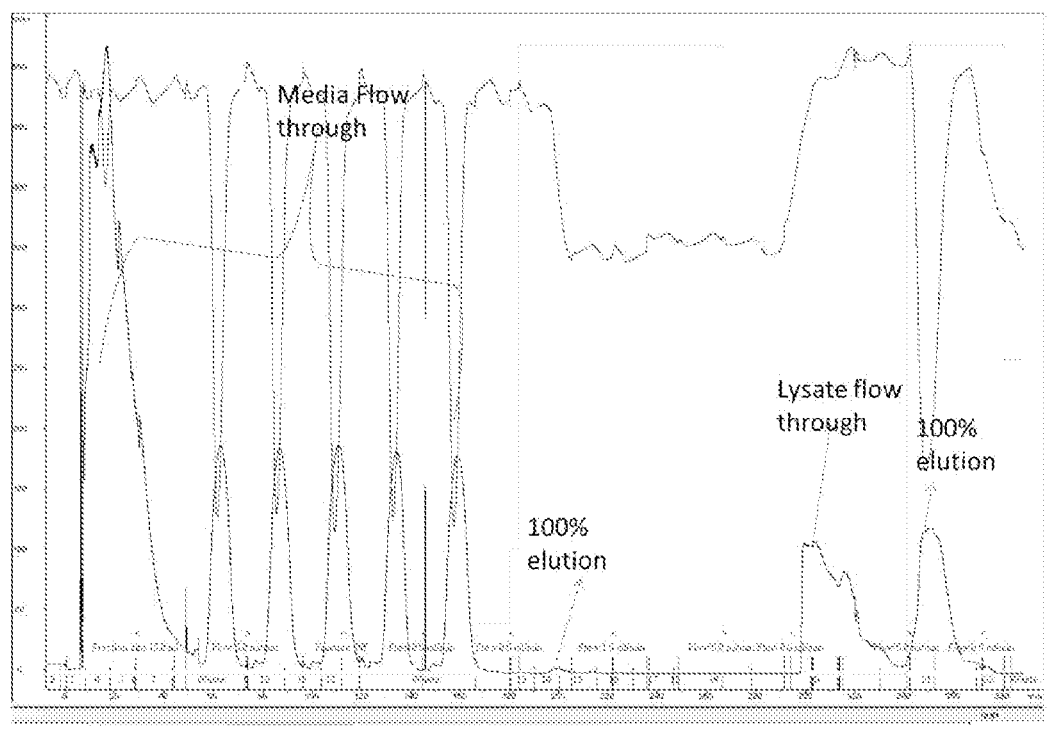
FIG. 3 is a graph of eluent from a $B_{12}$ column on which cell extract containing an expressed modified haptocorrin protein was loaded.
Figure 4:
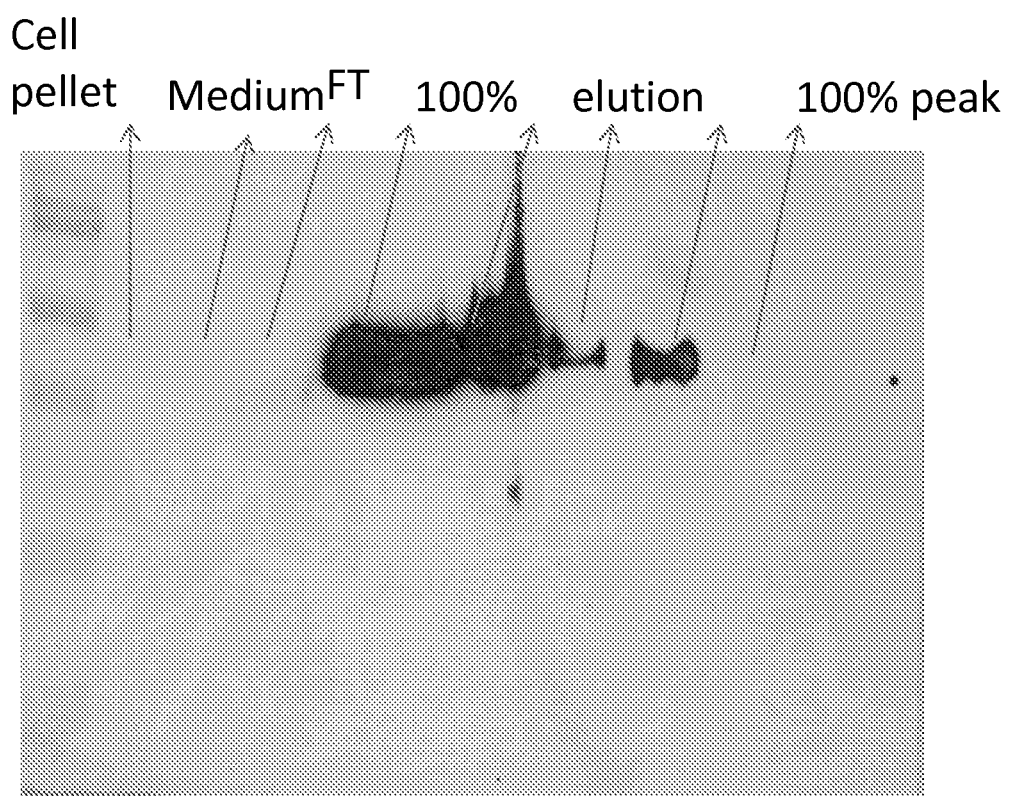
FIG. 4 is an image of eluent from the column of FIG. 3 testing positive for haptocorring using a haptocorrin primary antibody.

According to one embodiment, to test the expression of modified haptocorrin sequence 1 (YNHCZn), the modified gene (e.g., SEQ ID NO: 1) was expressed in insect cells The cell extract (containing the modified haptocorrin) was loaded onto a $B_{12}$ column and then eluted (shown in FIG. 3). The eluent was then tested for the presence of haptocorrin using a haptocorrin primary antibody, and positive results (see FIG. 4) indicated that the insect cell expressed modified haptocorrin sequence 1 (YNHCZn) is indeed expressed, and that the modified protein is capable of binding $B_{12}$.

EXAMPLE 5

Modified Haptocorrin Sequence 2 (HCZn2b)

As described herein, and in accordance with an embodiment, the human haptocorrin protein encoded by the TCN1 gene can be modified to include one or more zinc-binding sites. Another embodiment of a modified TCN1 gene containing a zinc-binding site sequence is SEQ ID NO: 4, which contains the zinc-binding site sequence MTSTTLVKCA-CEPCLCNVDPSKAIDRNGLYYCSEACADGHTGGSK-GCGHTGCNCHG (SEQ ID NO: 5) which is a SmtA metallothionein sequence. Metallothioneins are small, cysteine-rich proteins that are extremely good at binding metal ions. For example, the SmtA gene from *Synechococcus* binds zinc ions extremely well. According to this embodiment, the 168-nucleotide sequence encoding for this zinc-binding sequence is inserted between nucleotides 426 and 427 of human haptocorrin, and results in expression of the modified human haptocorrin protein identified by SEQ ID NO: 6.

EXAMPLE 6

Testing of Efficacy of Zinc Binding Complex

Once zinc binding sequences that can outcompete phytin are selected, those sequences can be incorporated into IF or haptocorrin, so that the resulting zinc binding complex may be tested for efficacy in humans using animal models. For example, the zinc binding complex may be orally administered along with zinc and phytin to a test group, and just the zinc and phytin delivered orally to a control group. Blood may then be drawn from both groups over a predetermined period of time to determine whether the administration of the zinc binding complex improves uptake of zinc in the presence of phytin.

Although the present invention has been described in connection with a preferred embodiment, it should be understood that modifications, alterations, and additions can be made to the invention without departing from the scope of the invention as defined by the claims.

What is claimed is:

1. A nucleic acid molecule comprising a chimeric gene derived from human haptocorrin comprising a first sequence encoding a first region of haptocorrin, a second sequence encoding a zinc-binding site, and a third sequence encoding a second region of haptocorrin, wherein said nucleic acid molecule is selected from the group consisting of SEQ ID NO: 1 and SEQ ID NO: 4.

2. A polypeptide comprising a chimeric protein derived from human haptocorrin, the polypeptide comprising a zinc-binding site located between a first region of haptocorrin and a second region of haptocorrin, wherein said polypeptide is selected from the group consisting of SEQ ID NO: 3 and SEQ ID NO: 6.

3. The polypeptide of claim 2, wherein said polypeptide is capable of reversibly binding zinc.

4. A method of producing functional human haptocorrin which binds to zinc, comprising the steps of:
   modifying a human TCN1 gene to comprise one or more zinc-binding site sequences, wherein said modified human TCN1 gene is selected from the group consisting of SEQ ID NO: 1 and SEQ ID NO: 4;
   constructing a vector comprising said modified human TCN1 gene; and
   introducing said vector into a host cell for a time and under conditions sufficient for expression of said functional human haptocorrin.

5. The method of claim 4, wherein said functional human haptocorrin comprises a polypeptide sequence selected from the group consisting of SEQ ID NO: 3 and SEQ ID NO: 6.

6. The method of claim 4, further comprising the step of isolating said expressed functional human haptocorrin.

7. The method of claim 6, further comprising the step of incubating said isolated human haptocorrin with zinc.

8. A method of binding and releasing zinc using a chimeric protein, comprising the steps of:
   providing a chimeric protein derived from human haptocorrin, the chimeric protein comprising a zinc-binding site located between a first region of haptocorrin and a second region of haptocorrin, wherein said chimeric protein is selected from the group consisting of SEQ ID NO: 3 and SEQ ID NO: 6;
   binding said chimeric protein to zinc; and
   administering said zinc-bound chimeric protein orally.

* * * * *

SEQUENCE LISTING

```
<160> NUMBER OF SEQ ID NOS: 6

<210> SEQ ID NO 1
<211> LENGTH: 1308
<212> TYPE: DNA
<213> ORGANISM: Artificial Sequence
<220> FEATURE:
<223> OTHER INFORMATION: Human TCN1 gene modified to include a central
      zinc-binding site

<400> SEQUENCE: 1
atgcgccaga gccatcagct gcccctggtc ggactgctgc tgtttagttt catcccaagt      60
cagctgtgcg agatttgcga agtgtctgag gaaaattaca tcaggctgaa gccactgctg     120
aacacaatga ttcagagcaa ttataaccgc ggcacttccg ccgtgaatgt ggtcctgtct     180
ctgaagctgg tcggcatcca gattcagact ctgatgcaga aaatgatcca gcagattaag     240
tacaacgtga aaagcagact gtccgatgtc agctccgggg agctggccct gatcattctg     300
gctctgggag tgtgccgcaa tgccgaggaa aacctgatct acgattatca cctgattgac     360
aagctggaga acaagttcca ggcagagatc gaaaatatgg aagcacataa cgggacacca     420
ctgcgagacg cagatgctga cagactgtct ctggacgtgc tggccctgtg cctgttcaat     480
ggcaactact ccaccgctga ggtggtcaac cacttcacac tgaaaataa gaactactac      540 ttcggctctc agtttagtgt ggatactggg gcaatggccg tgctggctct gacctgtgtc     600
aagaaatccc tgatcaatgg gcagattaag gcagacgaag gaagtctgaa aaacatctca     660
atctacacca agagcctggt ggaaaaaatc ctgagtgaga agaaagaaaa tggactgatt     720
ggcaacactt tctccaccgg cgaggctatg caggcactgt tcgtgtctag tgattactac     780
aacgaaaacg actggaattg ccagcagaca ctgaacactg tgctgaccga gatcagccag     840
ggagcatttt ctaatccaaa cgccgctgca caggtgctgc cagcactgat gggcaagacc     900
ttcctggata ttaacaagga ctcaagctgt gtgtccgctt ctgggaattt taacatcagc     960
gcagatgagc ccattaccgt cacacccct gacagtcagt catacatctc agtgaattat     1020
agcgtcagga ttaacgagac atacttcact aatgtgaccg tcctgaacgg cagcgtgttt    1080
ctgtctgtca tggaaaaggc tcagaaaatg aacgatacaa tcttcggctt tactatggag    1140
gaacgaagct ggggacctta catcacctgc attcagggcc tgtgtgccaa caataacgac    1200
cggacatatt gggagctgct gagtggcggg gaaccactgt cacagggcgc agggagttat    1260
gtcgtgagaa atggagaaaa tctggaagtg aggtggagca aatactga                 1308

<210> SEQ ID NO 2
<211> LENGTH: 7
<212> TYPE: PRT
<213> ORGANISM: Artificial Sequence
<220> FEATURE:
<223> OTHER INFORMATION: Zinc-binding site protein sequence based on
      conventional zinc-binding site sequences

<400> SEQUENCE: 2

Arg Asp Ala Asp Ala Asp Arg
1               5
```

-continued

```
<210> SEQ ID NO 3
<211> LENGTH: 435
<212> TYPE: PRT
<213> ORGANISM: Artificial Sequence
<220> FEATURE:
<223> OTHER INFORMATION: Protein expressed by the human TCN1 gene
      modified to include a central zinc-binding site

<400> SEQUENCE: 3

Met Arg Gln Ser His Gln Leu Pro Leu Val Gly Leu Leu Phe Ser
1               5                   10                  15

Phe Ile Pro Ser Gln Leu Cys Glu Ile Cys Glu Val Ser Glu Glu Asn
            20                  25                  30

Tyr Ile Arg Leu Lys Pro Leu Leu Asn Thr Met Ile Gln Ser Asn Tyr
        35                  40                  45

Asn Arg Gly Thr Ser Ala Val Asn Val Val Leu Ser Leu Lys Leu Val
    50                  55                  60

Gly Ile Gln Ile Gln Thr Leu Met Gln Lys Met Ile Gln Gln Ile Lys
65                  70                  75                  80

Tyr Asn Val Lys Ser Arg Leu Ser Asp Val Ser Ser Gly Glu Leu Ala
                85                  90                  95

Leu Ile Ile Leu Ala Leu Gly Val Cys Arg Asn Ala Glu Glu Asn Leu
            100                 105                 110

Ile Tyr Asp Tyr His Leu Ile Asp Lys Leu Glu Asn Lys Phe Gln Ala
        115                 120                 125

Glu Ile Glu Asn Met Glu Ala His Asn Gly Thr Pro Leu Arg Asp Ala
    130                 135                 140

Asp Ala Asp Arg Leu Ser Leu Asp Val Leu Ala Leu Cys Leu Phe Asn
145                 150                 155                 160

Gly Asn Tyr Ser Thr Ala Glu Val Val Asn His Phe Thr Pro Glu Asn
                165                 170                 175

Lys Asn Tyr Tyr Phe Gly Ser Gln Phe Ser Val Asp Thr Gly Ala Met
            180                 185                 190

Ala Val Leu Ala Leu Thr Cys Val Lys Ser Leu Ile Asn Gly Gln
        195                 200                 205

Ile Lys Ala Asp Glu Gly Ser Leu Lys Asn Ile Ser Ile Tyr Thr Lys
    210                 215                 220

Ser Leu Val Glu Lys Ile Leu Ser Glu Lys Lys Glu Asn Gly Leu Ile
225                 230                 235                 240

Gly Asn Thr Phe Ser Thr Gly Glu Ala Met Gln Ala Leu Phe Val Ser
                245                 250                 255

Ser Asp Tyr Tyr Asn Glu Asn Asp Trp Asn Cys Gln Gln Thr Leu Asn
            260                 265                 270

Thr Val Leu Thr Glu Ile Ser Gln Gly Ala Phe Ser Asn Pro Asn Ala
        275                 280                 285

Ala Ala Gln Val Leu Pro Ala Leu Met Gly Lys Thr Phe Leu Asp Ile
    290                 295                 300

Asn Lys Asp Ser Ser Cys Val Ser Ala Ser Gly Asn Phe Asn Ile Ser
305                 310                 315                 320

Ala Asp Glu Pro Ile Thr Val Thr Pro Pro Asp Ser Gln Ser Tyr Ile
                325                 330                 335

Ser Val Asn Tyr Ser Val Arg Ile Asn Glu Thr Tyr Phe Thr Asn Val
            340                 345                 350

Thr Val Leu Asn Gly Ser Val Phe Leu Ser Val Met Glu Lys Ala Gln
        355                 360                 365
```

```
Lys Met Asn Asp Thr Ile Phe Gly Phe Thr Met Glu Glu Arg Ser Trp
    370                 375                 380

Gly Pro Tyr Ile Thr Cys Ile Gln Gly Leu Cys Ala Asn Asn Asn Asp
385                 390                 395                 400

Arg Thr Tyr Trp Glu Leu Leu Ser Gly Gly Glu Pro Leu Ser Gln Gly
                405                 410                 415

Ala Gly Ser Tyr Val Val Arg Asn Gly Glu Asn Leu Glu Val Arg Trp
            420                 425                 430

Ser Lys Tyr
        435

<210> SEQ ID NO 4
<211> LENGTH: 1479
<212> TYPE: DNA
<213> ORGANISM: Artificial Sequence
<220> FEATURE:
<223> OTHER INFORMATION: Human TCN1 gene modified to include SmtA
      metallothionein zinc-binding sequence

<400> SEQUENCE: 4
```

| | | |
|---|---|---|
| atgcgtcaaa gccatcaact gccgctggtc ggtctgctgc tgttctcgtt tatcccgtca | 60 |
| caactgtgcg aaatctgcga agtctctgaa gaaaattata ttcgtctgaa accgctgctg | 120 |
| aacaccatga tccagtctaa ttacaaccgc ggcacgagtg ccgttaatgt ggttctgtcc | 180 |
| ctgaaactgg tcggtattca gatccaaacc ctgatgcaaa aaatgatcca gcaaatcaaa | 240 |
| tacaacgtca aatcacgtct gtcggatgtg agctctggcg aactggccct gattatcctg | 300 |
| gcactgggtg tgtgccgcaa tgcagaagaa aacctgattt atgattacca tctgatcgac | 360 |
| aaactggaaa acaaattcca ggctgaaatc gaaaacatgg aagcgcacaa cggtaccccg | 420 |
| ctgcgtatga cgtcaaccac gctggtgaaa tgcgcctgtg aaccgtgcct gtgtaatgtt | 480 |
| gatccgagca agcaattga ccgcaacggc ctgtattact gctcagaagc ttgtgcggat | 540 |
| ggtcataccg gcggttcgaa aggctgcggt catacgggct gcaattgtca cggtcgtctg | 600 |
| agtctggacg tgctggctct gtgtctgttt aatggcaact attccaccgc ggaagtcgtg | 660 |
| aaccacttca cgccggaaaa caaaaactat tactttggca gccagttctc tgttgatacc | 720 |
| ggtgccatgg cagtgctggc cctgacgtgt gtgaaaaaat ctctgattaa tggccaaatc | 780 |
| aaagcagacg aaggtagcct gaaaaacatt tctatctaca ccaaaagtct ggtggaaaaa | 840 |
| atcctgagcg agaaaaaaga aaacggcctg atcggtaaca cctttctac gggtgaagct | 900 |
| atgcaggcgc tgttcgttag ttccgattat acaatgaaaa cgactggaa ttgccagcaa | 960 |
| accctgaaca cggttctgac cgaaatttcc cagggcgctt tttcaaatcc gaacgcagca | 1020 |
| gcacaagtcc tgccggcact gatgggtaaa acctttctgg atatcaacaa agactcatcg | 1080 |
| tgtgtcagcg cctctggcaa tttcaacatt agcgcagatg aaccgatcac cgtgacgccg | 1140 |
| ccggacagtc agtcctatat tagtgtcaat tactccgtgc gcatcaacga aacgtatttt | 1200 |
| accaatgtga cggttctgaa cggttcagtt ttcctgtcgg tcatggaaaa agcccagaaa | 1260 |
| atgaacgata ccattttttgg cttcacgatg gaagaacgta gctggggccc gtatattacc | 1320 |
| tgcatccagg gtctgtgtgc taacaataac gatcgcacct actgggaact gctgtctggt | 1380 |
| ggtgaaccgc tgtcgcaagg tgcaggtagc tatgttgtcc gcaatggcga aaacctggaa | 1440 |
| gtccgttgga gcaaatacca ccaccaccac caccactaa | 1479 |

```
<210> SEQ ID NO 5
<211> LENGTH: 56
```

```
<212> TYPE: PRT
<213> ORGANISM: Unknown
<220> FEATURE:
<223> OTHER INFORMATION: Synechococcus species

<400> SEQUENCE: 5

Met Thr Ser Thr Thr Leu Val Lys Cys Ala Cys Glu Pro Cys Leu Cys
1               5                   10                  15

Asn Val Asp Pro Ser Lys Ala Ile Asp Arg Asn Gly Leu Tyr Tyr Cys
            20                  25                  30

Ser Glu Ala Cys Ala Asp Gly His Thr Gly Gly Ser Lys Gly Cys Gly
        35                  40                  45

His Thr Gly Cys Asn Cys His Gly
    50                  55

<210> SEQ ID NO 6
<211> LENGTH: 492
<212> TYPE: PRT
<213> ORGANISM: Artificial Sequence
<220> FEATURE:
<223> OTHER INFORMATION: Protein expressed by the human TCN1 gene
      modified to include SmtA metallothionein zinc-binding sequence

<400> SEQUENCE: 6

Met Arg Gln Ser His Gln Leu Pro Leu Val Gly Leu Leu Leu Phe Ser
1               5                   10                  15

Phe Ile Pro Ser Gln Leu Cys Glu Ile Cys Glu Val Ser Glu Glu Asn
            20                  25                  30

Tyr Ile Arg Leu Lys Pro Leu Leu Asn Thr Met Ile Gln Ser Asn Tyr
        35                  40                  45

Asn Arg Gly Thr Ser Ala Val Asn Val Val Leu Ser Leu Lys Leu Val
    50                  55                  60

Gly Ile Gln Ile Gln Thr Leu Met Gln Lys Met Ile Gln Gln Ile Lys
65                  70                  75                  80

Tyr Asn Val Lys Ser Arg Leu Ser Asp Val Ser Gly Glu Leu Ala
                85                  90                  95

Leu Ile Ile Leu Ala Leu Gly Val Cys Arg Asn Ala Glu Glu Asn Leu
            100                 105                 110

Ile Tyr Asp Tyr His Leu Ile Asp Lys Leu Glu Asn Lys Phe Gln Ala
        115                 120                 125

Glu Ile Glu Asn Met Glu Ala His Asn Gly Thr Pro Leu Arg Met Thr
    130                 135                 140

Ser Thr Thr Leu Val Lys Cys Ala Cys Glu Pro Cys Leu Cys Asn Val
145                 150                 155                 160

Asp Pro Ser Lys Ala Ile Asp Arg Asn Gly Leu Tyr Tyr Cys Ser Glu
                165                 170                 175

Ala Cys Ala Asp Gly His Thr Gly Gly Ser Lys Gly Cys Gly His Thr
            180                 185                 190

Gly Cys Asn Cys His Gly Arg Leu Ser Leu Asp Val Leu Ala Leu Cys
        195                 200                 205

Leu Phe Asn Gly Asn Tyr Ser Thr Ala Glu Val Val Asn His Phe Thr
    210                 215                 220

Pro Glu Asn Lys Asn Tyr Tyr Phe Gly Ser Gln Phe Ser Val Asp Thr
225                 230                 235                 240

Gly Ala Met Ala Val Leu Ala Leu Thr Cys Val Lys Lys Ser Leu Ile
                245                 250                 255

Asn Gly Gln Ile Lys Ala Asp Glu Gly Ser Leu Lys Asn Ile Ser Ile
```

-continued

```
                     260                 265                 270
Tyr Thr Lys Ser Leu Val Glu Lys Ile Leu Ser Glu Lys Lys Glu Asn
            275                 280                 285

Gly Leu Ile Gly Asn Thr Phe Ser Thr Gly Glu Ala Met Gln Ala Leu
            290                 295                 300

Phe Val Ser Ser Asp Tyr Tyr Asn Glu Asn Asp Trp Asn Cys Gln Gln
305                 310                 315                 320

Thr Leu Asn Thr Val Leu Thr Glu Ile Ser Gln Gly Ala Phe Ser Asn
            325                 330                 335

Pro Asn Ala Ala Ala Gln Val Leu Pro Ala Leu Met Gly Lys Thr Phe
            340                 345                 350

Leu Asp Ile Asn Lys Asp Ser Ser Cys Val Ser Ala Ser Gly Asn Phe
            355                 360                 365

Asn Ile Ser Ala Asp Glu Pro Ile Thr Val Thr Pro Pro Asp Ser Gln
            370                 375                 380

Ser Tyr Ile Ser Val Asn Tyr Ser Val Arg Ile Asn Glu Thr Tyr Phe
385                 390                 395                 400

Thr Asn Val Thr Val Leu Asn Gly Ser Val Phe Leu Ser Val Met Glu
            405                 410                 415

Lys Ala Gln Lys Met Asn Asp Thr Ile Phe Gly Phe Thr Met Glu Glu
            420                 425                 430

Arg Ser Trp Gly Pro Tyr Ile Thr Cys Ile Gln Gly Leu Cys Ala Asn
            435                 440                 445

Asn Asn Asp Arg Thr Tyr Trp Glu Leu Leu Ser Gly Gly Glu Pro Leu
            450                 455                 460

Ser Gln Gly Ala Gly Ser Tyr Val Val Arg Asn Gly Glu Asn Leu Glu
465                 470                 475                 480

Val Arg Trp Ser Lys Tyr His His His His His His
            485                 490
```